United States Patent [19]
Ramachandran et al.

[11] Patent Number: 4,590,010
[45] Date of Patent: May 20, 1986

[54] SUBSTITUTED NAPHTHOIC ACID PROCESS

[75] Inventors: Venkataraman Ramachandran; Robert I. Davidson; John R. Maloney, all of Baton Rouge, La.

[73] Assignee: Ethyl Corporation, Richmond, Va.

[21] Appl. No.: 724,474

[22] Filed: Apr. 18, 1985

[51] Int. Cl.[4] ............... C07C 121/75; C07C 63/36
[52] U.S. Cl. ..................... 558/341; 560/56; 562/467
[58] Field of Search ............... 260/465 F; 562/467

[56] References Cited

U.S. PATENT DOCUMENTS 4,408,077  10/1983  Sestanj et al. ............... 568/441
4,439,617   3/1984  Sestanj et al. ............... 560/39
4,536,343   8/1985  Ramachandran ............ 260/465 F

OTHER PUBLICATIONS

Sestanj et al., J. Med. Chem. vol. 27, pp. 255–256, (1984).
Matsui et al., Chemistry Letters, pp. 1719–1720, (1981).
Stork, J. Am. Chem. Soc., vol. 69, pp. 576–579, (1947).
Thomas et al., J. Am. Chem. Soc., vol. 70, pp. 331–334, (1948).
Papa, J. Am. Chem. Soc., vol. 71, pp. 3246–3247, (1949).
Nagata et al., Organic Syntheses, vol. 52, pp. 96–99, (1972).
Jacobs et al., J. Org. Chem., vol. 48, pp. 5134–5135, (1983).
March, Advanced Organic Chemistry, Second Edition, McGraw-Hill (New York), pp. 363–365 and 809–810.

Primary Examiner—Dolph H. Torrence
Attorney, Agent, or Firm—Donald L. Johnson; John F. Sieberth; Patricia J. Hogan

[57] ABSTRACT

6-Alkoxy-5-trifluoromethyl-1-naphthoic acids are prepared by (1) cyanating a 6-alkoxytetralone so as to form a 6-alkoxy-1-cyano-3,4-dihydronaphthalene, (2) converting the 6-alkoxy-1-cyano-3,4-dihydronaphthalene to a naphthoic acid precursor selected from a 6-alkoxy-1-cyanonaphthalene and a hydrocarbyl 6-alkoxy-1-naphthoate, (3) halogenating the naphthoic acid precursor to the corresponding 5-halo derivative, (4) trifluoromethylating the 5-halo derivative to replace the 5-halo substituent with a 5-trifluoromethyl group, and (5) hydrolyzing the resultant product to a 6-alkoxy-5-trifluoromethyl-1-naphthoic acid. In a preferred embodiment of the invention, the process is conducted so as to prepare 6-methoxy-5-trifluoromethyl-1-naphthoic acid, which, like the other products, is known to be useful as a pharmaceutical intermediate.

30 Claims, No Drawings

SUBSTITUTED NAPHTHOIC ACID PROCESS

FIELD OF INVENTION

This invention relates to 6-alkoxy-5-trifluoromethyl-1-naphthoic acids and more particularly to processes for preparing them.

BACKGROUND

As disclosed in Sestanj et al., *J. Med. Chem.*, 1984, Vol. 27, pp. 255-256 (Sestanj et al. I) and U.S. Pat. Nos. 4,408,077 (Sestanj et al. II) and 4,439,617 (Sestanj et al. III), it is known that 6-alkoxy-5-trifluoromethyl-1-naphthoic acids are useful as pharmaceutical intermediates and that they can be prepared by a variety of techniques. It is also known that the syntheses of Sestanj et al. I and III can be modified by conducting the trifluoromethylation step as in Matsui et al., *Chemistry Letters*, 1981, pp. 1719-1720, and that particularly good results are obtained when N,N-dimethylacetamide is employed as the solvent in this step.

The known techniques of synthesizing these pharmaceutical intermediates have their relative advantages and disadvantages, but there is still a need for a synthesis that would be more attractive as a commercial process.

SUMMARY OF INVENTION

An object of this invention is to provide a novel process for preparing 6-alkoxy-5-trifluoromethyl-1-naphthoic acids.

Another object is to provide such a process which has commercial advantages over known processes for preparing those naphthoic acids.

A further object is to provide novel compounds useful in the preparation of 6-alkoxy-5-trifluoromethyl-1-naphthoic acids.

These and other objects are attained by (1) cyanating a 6-alkoxytetralone so as to form a 6-alkoxy-1-cyano-3,4-dihydronaphthalene, (2) converting the 6-alkoxy-1-cyano-3,4-dihydronaphthalene to a naphthoic acid precursor selected from a 6-alkoxy-1-cyanonaphthalene and a hydrocarbyl 6-alkoxy-1-naphthoate, (3) halogenating the naphthoic acid precursor to the corresonding 5-halo derivative, (4) trifluoromethylating the 5-halo derivative to replace the 5-halo substituent with a 5-trifluoromethyl group, and (5) hydrolyzing the resultant product to a 6-alkoxy-5-trifluoromethyl-1-naphthoic acid.

DETAILED DESCRIPTION

Cyanation

6-Alkoxytetralones that can be used in the practice of the invention embrace all 6-alkoxytetralones capable of being converted to 6-alkoxy-5-trifluoromethyl-1-naphthoic acids by the present process, including the 6-alkoxytetralones wherein the 6-substituent is an alkoxy group containing 1-20 carbons or such an alkoxy group bearing an inert substituent such as a phenyl, alkylphenyl, or alkoxyphenyl group, etc. However, the preferred 6-alkoxytetralones are those wherein the alkoxy group is a lower alkoxy group (i.e., an alkoxy group containing 1-6 carbons), most preferably a straight-chain alkoxy group of 1-3 carbons or a branched-chain alkoxy group of 3 or 4 carbons, such as methoxy, ethoxy, 1-methylethoxy, butoxy, hexoxy, etc. A particularly preferred 6-alkoxytetralone is 6-methoxytetralone.

The 6-alkoxytetralones, when not commercially available, can be prepared by known techniques, e.g., the techniques which can be learned directly or analogized from the teachings of Stork, *Journal of the American Chemical Society*, Vol. 69, pp. 576-579 (1947); Thomas et al., *Journal of the American Chemical Society*, Vol. 70, pp. 331-334 (1948); and Papa, *Journal of the American Chemical Society*, Vol 71, pp. 3246-3247 (1949); as well as the references cited therein, the teachings of all of which are incorporated herein by reference.

As indicated above, the 6-alkoxytetralone is converted to a 6-alkoxy-1-cyano-3,4-dihydronaphthalene by a cyanation reaction. This type of reaction, as is known, involves the addition of a cyanide group to the starting material and the subsequent dehydroxylation or dehydration of the resultant intermediate to form the desired product. In the practice of the invention, this cyanation may be accomplished by the known techniques that require more than one step, e.g., the techniques of Nagata et al., *Organic Syntheses*, 1972, Vol. 52, pp. 96-99, and those of Jacobs et al., *Journal of Organic Chemistry*, 1983, Vol. 48, pp. 5134-5135, the teachings of which are incorporated herein by reference. However, in order for the advantages of the invention to be fully realized, it is preferably accomplished by a one-step technique.

This preferred method of preparing a 6-alkoxy-1-cyano3,4-dihydronaphthalene is unconventional but can be realized fairly simply by reacting the 6-alkoxytetralone with cyanide ion and a Lewis acid, such as hydrogen fluoride, a trialkylaluminum, or, more preferably, a metal halide, such as boron or aluminum trifluoride, triiodide, trichloride, or tribromide, tin tetrachloride, zinc dichloride, gallium trichloride, titanium tetrachloride, diethylaluminum chloride, ethylaluminum dichloride, ethoxyaluminum dichloride, diethoxyaluminum chloride, hydroxyaluminum dichloride, dihydroxyaluminum chloride, and other such compounds wherein at least one halogen is attached to a metal atom, any remaining valences of which are usually satisfied by hydroxy, hydrocarbyl, or hydrocarbyloxy groups, generally hydroxy or alkyl or alkoxy groups containing 1-10 carbons. The preferred Lewis acids are boron trifluoride and aluminum chloride, especially aluminum chloride. This ingredient of the reaction mixture is ordinarily employed in the amount of about 0.5-1.5, preferably about 1-1.1, mols per mol of the 6-alkoxytetralone, although smaller or larger amounts can be employed if desired.

In this preferred cyanation reaction, the cyanide ion may be provided by any known source of cyanide ion that is free of radicals which would stabilize the cyanohydrin that is believed to be initially formed in the reaction. However, it is most commonly provided by hydrogen cyanide, a tri- or tetraalkylammonium cyanide (generally such a compound containing up to about 50 carbons) such as trimethylammonium cyanide, tributylmethylammonium cyanide, tetrabutylammonium cyanide, etc., or a metal cyanide, such as cuprous cyanide or an alkali or alkaline earth metal cyanide such as lithium, sodium, potassium, rubidium, cesium, beryllium, magnesium, calcium, strontium, or barium cyanide. The sodium, potassium, and hydrogen cyanides are generally the preferred sources of cyanide ion. The amount of cyanide ion employed is not critical, but it is usually desirable to employ about 1-5, preferably about 1-2, mols of cyanide ion per mol of 6-alkoxytetralone to produce good yields of product.

Other ingredients that are suitably included in the reaction mixture in the preferred cyanation process are a solvent and a phase transfer catalyst. Solvents that may be employed include all solvents in which the reactants are soluble, such as aliphatic and aromatic hydrocarbons (e.g., toluene, xylenes, heptanes, and the like), chlorobenzene, nitrobenzene, etc.; but the preferred solvent is generally nitrobenzene. Particularly useful phase transfer catalysts are tetralkylammonium halides (generally such halides containing up to about 50 carbons), preferably bromides and chlorides, such as tetrabutylammonium bromide, tributylmethylammonium chloride, etc. When employed, the catalyst is used in a catalytic amount, e.g., about 2-6% by weight of the 6-alkoxytetralone; and its use sometimes seems to permit the attainment of higher yields than can be obtained in its absence.

In the practice of the preferred cyanation reaction, the ingredients of the reaction mixture may be combined in any suitable manner, preferably with the solids in finely-divided form, and heated at a suitable temperature, e.g., about 60°-120° C., preferably about 90° C., to produce the desired product. Lower temperatures can be used but are less desirable because of their leading to slower reactions; higher temperatures are apt to be undesirable because of the tendency for by-products to be formed at the higher temperatures. The time required to obtain good yields varies with the temperature but is frequently in the range of about 4-10 hours.

It is sometimes preferred to combine the ingredients by prestirring the cyanide ion source, the Lewis acid, and a solvent before combining these ingredients with the 6-alkoxytetralone, and it appears to be desirable to maintain the temperature of these ingredients below 60° C., e.g., at about 10°-50° C., conveniently at about 20°-30° C., until the addition of the 6-alkoxytetralone has been completed.

It is also sometimes preferred to conduct the cyanation in the presence of a small amount of water and/or concentrated HCl—additives which appear to effect an activation of one or more of the reactants and increase yields. The particular amount of water and/or HCl employed is an activating amount, i.e., an amount insufficient to hydrolyze the Lewis acid completely, and may be provided simply by the water naturally present in one or more of the aforementioned ingredients of the reaction mixture. When it is desired to employ additional water and/or HCl, the added amount is generally in the range of about 0.1-1.0 mol per mol of the 6-alkoxytetralone.

Conversion of
6-Alkoxy-1-Cyano3,4-Dihydronaphthalene

As mentioned above, the cyanation of the 6-alkoxytetralone results in the formation of a 6-alkoxy-1-cyano-3,4-dihydronaphthalene, which is then converted to a naphthoic acid precursor selected from a 6-alkoxy-1-cyanonaphthalene and a hydrocarbyl 6-alkoxy-1-naphthoate. The 6-alkoxy-1-cyano-3,4-dihydronaphthalene formed in the cyanation step may be recovered by conventional means prior to being subjected to this conversion, but such a recovery is unnecessary, inconvenient, and therefore not preferred.

When the naphthoic acid precursor desired is a 6-alkoxy1-cyanonaphthalene, the conversion is simply an aromatization which may be accomplished by techniques already known to the art, e.g., heating the reaction mixture containing the 6-alkoxy-1-cyano-3,4-dihydronaphthalene, preferably at reflux temperatures, in the presence of a palladium-on-carbon, platinum, nickel, or other dehydrogenation catalyst; aromatizing the compound with sulfur, etc. It is ordinarily preferred to aromatize the compound by dehydrogenation in the presence of a palladium-on-carbon catalyst.

When the naphthoic acid precursor desired is a hydrocarbyl 6-alkoxy-1-naphthoate, the 6-alkoxy-1-cyano-3,4-dihydronaphthalene is first converted to a 6-alkoxy-1-cyanonaphthalene as described above, then hydrolyzed to the corresponding 6-alkoxy-1-naphthoic acid, and then esterified by known techniques, such as the hydrolyzation and esterification techniques taught in March, *Advanced Organic Chemistry*, Second Edition, McGraw-Hill (New York), pp. 809-810 and 363-365, the teachings of which are incorporated herein by reference. In a preferred embodiment of the invention, the 6-alkoxy-1-cyanonaphthalene is hydrolyzed in the presence of a base such as sodium hydroxide and then esterified with an appropriate alcohol, generally an alcohol corresponding to the formula ROH wherein R is a saturated hydrocarbyl group (i.e., a hydrocarbyl group that is free of aliphatic unsaturation) such as an alkyl, cycloalkyl, aryl, alkaryl, or aralkyl group containing 1-10 carbons, in the presence of an acid such as HCl, sulfuric acid, etc. Ordinarily the alcohol employed in the esterification reaction is methanol.

Halogenation

Regardless of whether the desired naphthoic acid precursor formed in the conversion step is a 6-alkoxy-1-cyanonaphthalene or a hydrocarbyl 6-alkoxy-1-naphthoate, it is then halogenated to a corresponding 5-halo derivative, i.e., a 6-alkoxy-5-halo-1-cyanonaphthalene or a hydrocarbyl 6-alkoxy-5-halo-1-naphthoate, generally after having been isolated from its synthesis mixture by conventional techniques. This halogenation may be a fluorination, chlorination, bromination, or iodination and may be accomplished by known techniques, such as the techniques disclosed in March, pp. 482-484, and the references cited therein, the teachings of all of which are incorporated herein by reference. However, since the 5-halo compounds are prepared as precursors to 5-trifluoromethyl compounds, and at least the preferred trifluoromethylation techniques are most satisfactorily performed on iodo and bromo compounds, the preferred halogenation techniques are those for the iodination or bromination of aromatic compounds.

When a 5-iodo compound is desired, it is ordinarily preferred to prepare the product by reacting the 6-alkoxy-1-cyanonaphthalene or hydrocarbyl 6-alkoxy-1-naphthoate with iodine/iodic acid as in March, Sestanj et al. I, and Sestanj et al. III (especially Example 1*f*), the teachings of all of which are incorporated herein by reference. However, other oxidizing agents, such as hydrogen peroxide, etc., can be used instead of iodic acid, or the iodic acid may be generated in situ instead of being incorporated per se.

When a 5-bromo compound is desired, it is prepared so easily that it is not even necessary to employ a catalyst, though the conventional bromination catalysts could be employed without adversely affecting the reaction. Thus, it is ordinarily preferred to prepare the compound simply by reacting the 6-alkoxy-1-cyanonaphthalene or hydrocarbyl 6-alkoxy-1-naphtholate with bromine in a suitable solvent, e.g., a halogenated alkane such as methylene chloride, ethylene bromide, carbon tetrachloride, etc., at any suitable temperature, e.g., about −5° C. to about 20° C. Lower reaction temperatures can be used but do not appear to offer any particular advantage, and higher temperatures are also utilizable but are conducive to the loss of bromine.

The use of a 6-alkoxy-1-cyanonaphthalene in the halogenation reaction is particularly advantageous, and it leads to the formation of a novel compound, i.e., a 6-alkoxy-5-halo-1-cyanonaphthalene wherein the alkoxy substituent is the alkoxy group corresponding to the alkoxy substituent in the initial 6-alkoxytetralone, generally, as indicated above, an alkoxy group containing 1-20, preferably 1-6, carbons, and most preferably methoxy; and the halo substituent is fluoro, chloro, bromo, or iodo, preferably bromo or iodo. These novel compounds are advantageous in that they have higher melting points and lower degrees of solubility than the corresponding esters.

Trifluoromethylation

The 5-halo derivative prepared in the halogenation step, generally after being recovered by conventional techniques, may be converted to the corresponding 5-trifluoromethyl compound by known trifluoromethylation techniques, e.g., the techniques taught in Sestanj et al. I, Sestanj et al. II, Sestanj et al. III (especially Example 1h), Matsui et al., and the references cited therein, the teachings of all of which are incorporated herein by reference. In a preferred embodiment of the invention, the 5-halo derivative is trifluoromethylated, as in Matsui et al., by reacting it with a trifluoroacetate salt, preferably sodium trifluoroacetate, at a suitable temperature, conveniently at reflux temperatures, in the presence of cuprous iodide and a dipolar aprotic solvent, such as N-methylpyrrolidone, N,N-dimethylformamide, N,N-dimethylacetamide, hexamethylphosphoric triamide, etc., most desirably N,N-dimethylacetamide.

As in the halogenation reaction, the use of the nitrile reactants is preferred to the use of the ester reactants, and this use leads to the formation of novel compounds which have the advantages of higher melting points and lower degrees of solubility than the corresponding esters. In this case, the novel compounds are the 6-alkoxy-5-trifluoromethyl-1-cyanonaphthalenes corresponding to the 6-alkoxy-5- halo-1-cyanonaphthalenes described in the previous section.

Hydrolysis

Hydrolysis of the 6-alkoxy-5-trifluoromethyl-1-cyanonaphthalene or hydrocarbyl 6-alkoxy-5-trifluoromethyl-1-naphthoate to the corresponding acid is accomplished by conventional techniques, such as those described above in connection with the hydrolysis of 6-alkoxy-1-cyanonaphthalenes, generally by reaction with water in the presence of a base such as sodium or potassium hydroxide.

After completion of the hydrolysis step, the resultant 6-alkoxy-5-trifluoromethyl-1-naphthoic acid may be recovered by conventional means and/or converted to a desired derivative, such as the pharmaceutical materials taught in the Sestanj et al. references.

The invention is particularly advantageous as a commercially-attractive process for preparing 6-alkoxy-5-trifluoromethyl-1-naphthoic acids, especially 6-methoxy-5-trifluoromethyl-1-naphthoic acid, which can then be converted to other products, such as tolrestat and similar pharmaceuticals. The aspect of the invention wherein the nitrile formed in the cyanation step is not converted to an acid until the trifluoromethyl group has been attached to the ring is preferred because of the greater reactivities of the nitrile intermediates in the halogenation and trifluoromethylation steps and because of the greater ease with which the intermediates can be recovered. However, both aspects have economic advantages over known techniques of preparing 6-alkoxy-5-trifluoromethyl-1-naphthoic acids.

The following examples are given to illustrate the invention and are not intended as a limitation thereof.

A. CYANATION REACTIONS

EXAMPLE I

A mixture of 1.3 g of dry $AlCl_3$, 0.64 g of dry NaCN, and 87 mg of tetrabutylammonium bromide (TBAB) in 8.7 ml of dry nitrobenzene (NB) was stirred for two hours under a nitrogen atmosphere. Then 1.53 g of 6-methoxytetralone (6-MT) were added to provide a reaction mixture containing the 6-MT, NaCN, and $AlCl_3$ in a mol ratio of 1/1.5/1.1 and containing 5.6% of TBAB, based on the weight of 6-MT. The reaction mixture was stirred at 90° C. for 10 hours to form 6-methoxy-1-cyano-3,4-dihydronaphthalene (6-MCDN). After workup the VPC ratio of 6-MT/6-MCDN was determined to be 8/92. The process resulted in an 85% isolated yield of 6-MCDN.

EXAMPLE II

Example I was essentially repeated except that the $AlCl_3$/NaCN/TBAB/NB mixture was not subjected to the two hour stirring period prior to the addition of the 6-MT. After workup the VPC ratio of 6-MT/6-MCDN was determined to be 41/59.

EXAMPLE III

A mixture of 1.56 g of boron trifluoride etherate, 0.98 g of NaCN, and 100 mg of TBAB in 10 ml of NB was stirred for two hours. Then 1.76 g of 6-MT were added to provide a reaction mixture containing the 6-MT, NaCN, and $BF_3$ in a mol ratio of ½/1.1. The mixture was heated at 90° C. for two hours and then at 120° C. for six hours to form 6-MCDN. Analysis showed the 6-MT/6-MCDN ratio to be 5/4.

EXAMPLE IV

An 8.47 g portion of $AlCl_3$ was added under nitrogen in a dry box to a suitable reaction vessel, followed by the addition of a 50 ml portion of dry NB. The resulting mixture was stirred for 15 minutes, after which 5.57 g of powdered NaCN and 0.50 g of dry TBAB were successively added. The resulting yellow slurry was stirred for two hours. Then 10 g of distilled 6-MT were added to provide a green slurry containing the 6-MT, NaCN, $AlCl_3$, and TBAB in a mol ratio of ½/1.1/0.03, and the reaction mixture was heated to 90° C. and maintained at that temperature for six hours. Analysis of the slurry after completion of the reaction showed it to contain 78.8% 6-MT and 19.5% 6-MCDN by GC area %.

EXAMPLE V

Example IV was essentially repeated except that 0.25 g of concentrated HCl was added to the reaction mixture after the addition of the TBAB had been completed, and the reaction mixture was maintained at 90° C. for only four hours. Analysis of the final reaction mixture showed it to contain 7 area % 6-MT and 89.4 area % 6-MCDN.

EXAMPLE VI

Example IV was essentially repeated except that three drops of water were added to the reaction mixture after the addition of the TBAB had been completed. Analysis of the final reaction mixture showed it to contain 4.4 area % 6-MT and 90.5 area % 6-MCDN.

EXAMPLE VII

A solution of 22.7 g of anhydrous AlCl3 in 100 ml of NB was cooled to 10° C. in an ice bath, after which 6.9 g of liquid HCN were added. The mixture was stirred vigorously and 30 g of 6-MT were added to provide a reaction mixture containing the 6-MT, HCN, and AlCl3 in a mol ratio of 1/1.5/1. When the 6-MT had completely dissolved, the mixture was transferred to an autoclave and heated at 70° C. for ten hours. After cooling, the contents of the autoclave were removed and treated with 100 ml of dilute HCl and 100 ml of methylene chloride. The mixture was shaken in a separatory funnel and allowed to stand for phase separation. The lower organic layer was removed and concentrated on a rotary evaporator to remove methylene chloride. GC investigation (internal standard method) of the nitrobenzene solution showed an 88% yield of 6-MCDN.

B. CONVERSIONS OF 6-ALKOXY-1-CYANO-3,4-DIHYDRONAPHTHALENES

EXAMPLE VIII

A crude 6-MCDN in NB prepared essentially as in Example I was treated with 5% (based on the weight of the original 6-MT) of 5 % Pd/C at 150°-220° C. for 10 hours. The process resulted in the conversion of 97% of the 6-MCDN to 6-methoxy-1-cyanonaphthalene (6-MCN).

EXAMPLE IX

Part A

A mixture of 5 g of 6-MCN, 10 g of 50% NaOH, and 50 mg of TBAB was stirred for 2-3 hours at 120°-130° C. (HPLC showed that the reaction was completed in two hours.) After workup HPLC analysis showed that the process had resulted in a 96% yield of 6-methoxynaphthoic acid.

Part B

A mixture of 9.1 g of 6-methoxynaphthoic acid and 7.2 g of anhydrous potassium carbonate in 45 ml of acetone was heated to 50°-55° C. for 15 minutes, and 4.5 ml of dimethyl sulfate were then slowly dripped in over a period of 15 minutes. The mixture was then heated at reflux for one hour and cooled to room temperature, after which all the acetone was stripped under vacuum. After workup, it was determined that the process resulted in the formation of 8.85 g of methyl 6-methoxynaphthoate having an HPLC purity of 83.3%.

C. HALOGENATIONS

EXAMPLE X

Methyl 6-methoxyl-1-naphthoate can be iodinated to methyl 5-iodo-6-methoxy-1-naphthoate by treatment with iodine and iodic acid in the presence of acetic and sulfuric acids as in Example 1f of Sestanj et al. III.

EXAMPLE XI

A solution of 5 g of 6-MCN in methylene chloride was brominated with 1.1 molar equivalents of bromine at −5° C. to provide an 89% yield of crude 5-bromo-6-methoxy-1-cyanonaphthalene.

EXAMPLE XII

A solution of 5 g of 6-MCN in methylene chloride was brominated with 1.1 molar equivalents of bromine at 20° C. to provide a 95% yield of crude 5-bromo-6-methoxy-1-cyanonaphthalene.

EXAMPLE XIII

Concentrated sulfuric acid (2.6 g) was slowly dripped into a stirred mixture of 18.7 g of crude 6-MCN, 10.3 g of iodine, 4.06 g of iodic acid and 172 ml of aqueous acetic acid over a period of 10 minutes. The mixture was then slowly warmed to 70°-75° C. over a period of one hour and maintained at that temperature for another hour. After cooling the mixture was worked up to provide a 93% isolated yield of 5-iodo-6-methoxy-1-cyanonaphthalene.

D. TRIFLUOROMETHYLATIONS

EXAMPLE XIV

Methyl 5-iodo-6-methoxy-1-naphthoate can be trifluoromethylated with trifluoromethyliodide in the presence of copper powder and pyridine as in Example 1h of Sestanj et al. III to prepare methyl 5-trifluoromethyl-6-methoxy-1-naphthoate.

EXAMPLE XV

A 6.15 g portion of cuprous iodide and 5.5 g of sodium trifluoroacetate were added to a stirred solution of 4.2 g of 98% pure 5-bromo-6-methoxy-1-cyanonaphthalene in 25 ml of toluene. The resulting slurry was heated to reflux, and 10 ml of toluene were slowly distilled off. Then 100 ml of dimethylacetamide (DMAC) were added, and the resulting slurry was heated at reflux with distillation until the pot temperature rose to 154° C. The mixture was refluxed for six hours, at which point HPLC analysis indicated complete conversion of starting material. After workup the 6-methoxy-5-trifluoromethyl-1-cyanonaphthalene product (98.5% pure by HPLC) was isolated in 82% yield.

EXAMPLE XVI

A mixture of 5 g of 5-iodo-6-methoxy-1-cyanonaphthalene, 9.65 g of sodium, trifluoroacetate, and 6.15 g of cuprous iodide was stirred into 40 ml of toluene, after which about 30 ml of toluene was distilled over at atmospheric pressure. Then 100 ml of dry N-methylpyrrolidone (NMP) was added, and the mixture was heated at 150°-155° C. for four hours. At the end of the reaction, most of the NMP was distilled under vacuum at 80°-100° C. After workup the 6-methoxy-5-trifluoromethyl-1-cyanonaphthalene product was isolated in 73% yield.

EXAMPLE XVII

A mixture of 10 g of 5-iodo-6-methoxy-1-cyanonaphthalene, 11 g of sodium trifluoroacetate, and 12.33 g of cuprous iodide was stirred into 50 ml of toluene, after which about 20 ml of toluene was distilled over at 120°

C., 760 mm of pressure. Then 200 ml of dry DMAC were added, and the mixture was heated while distilling over another 10–15 ml until the temperature reached 152° C. The slurry was gently refluxed at 150°–155° C. for four hours and then cooled to 120° C. Another 1.1 g of sodium trifluoroacetate were added, and the reaction mixture was heated back up to 152° C. and stirred for two hours at 150°–155° C. At the end of the reaction, most of the DMAC was stripped under vacuum at a temperature below 80° C. After workup the 6-methoxy-5-trifluoromethyl-1-cyanonaphthalene was isolated in 90% yield.

E. HYDROLYSES

EXAMPLE XVIII

Methyl 5-trifluoromethyl-6-methoxy-1-naphthoate can be converted to 5-trifluoromethyl-6-methoxy-1-naphthoic acid by hydrolyzation with aqueous sodium hydroxide in the presence of methanol as in Example 1$h$ of Sestanj et al. III.

EXAMPLE XIX

A solution of 0.5 g of 6-methoxy-5-trifluoromethyl-1-cyanonaphthalene and 0.6 g of potassium hydroxide in 25 ml of a 20/5 mixture of methanol and water was charged into an autoclave, heated to 130° C. and stirred for 5-6 hours at an internal pressure of 90–100 psi. The reaction mixture was then cooled and worked up to provide a 98% recovered yield of 100% pure 6-methoxy-5-trifluoromethyl-1-naphthoic acid.

It is obvious that many variations can be made in the products and processes set forth above without departing from the spirit and scope of this invention.

What is claimed is:

1. A process which comprises (1) cyanating a 6-alkoxytetralone so as to form a 6-alkoxy-1-cyano-3,4-dihydronaphthalene, (2) converting the 6-alkoxy-1-cyano-3,4-dihydronaphthalene to a naphthoic acid precursor selected from a 6-alkoxy-1-cyanonaphthalene and a hydrocarbyl 6-alkoxy-1-naphthoate, (3) halogenating the naphthoic acid precursor to the corresponding 5-halo derivative, (4) trifluoromethylating the 5-halo derivative to replace the 5-halo substituent with a 5-trifluoromethyl group, and (5) hydrolyzing the resultant product to a 6-alkoxy-5-trifluoromethyl-1-naphthoic acid.

2. The process of claim 1 wherein the 6-alkoxytetralone is 6-methoxytetralone.

3. The process of claim 1 wherein the 6-alkoxytetralone is cyanated by reacting it with cyanide ion and a Lewis acid so as to form a 6-alkoxy-1-cyano-3,4-dihydronaphthalene.

4. The process of claim 3 wherein the cyanide ion is provided by hydrogen cyanide, a tri- or tetraalkylammonium cyanide, or a metal cyanide.

5. The process of claim 4 wherein the cyanide ion is provided by hydrogen cyanide.

6. The process of claim 4 wherein the cyanide ion is provided by a metal cyanide.

7. The process of claim 6 wherein the metal cyanide is an alkali metal cyanide.

8. The process of claim 7 wherein the alkali metal cyanide is sodium cyanide.

9. The process of claim 3 wherein the Lewis acid is a metal halide.

10. The process of claim 9 wherein the metal halide is aluminum chloride.

11. The process of claim 3 wherein the cyanation is conducted in the presence of an activating amount of water and/or concentrated HCl.

12. The process of claim 1 wherein the naphthoic acid precursor is a 6-alkoxy-1-cyanonaphthalene which is prepared by dehydrogenating the 6-alkoxy-1-cyano-3,4-dihydronaphthalene.

13. The process of claim 1 wherein the naphthoic acid precursor is a hydrocarbyl 6-alkoxy-1-naphthoate which is prepared by dehydrogenating the 6-alkoxy-1-cyano-3,4-dihydronaphthalene to a 6-alkoxy-1-cyanonaphthalene, hydrolyzing the 6-alkoxy-1-cyanonaphthalene, and esterifying the resultant 6-alkoxy-1-naphthoic acid.

14. The process of claim 1 wherein the 5-halo derivative is a 6-alkoxy-5-halo-1-cyanonaphthalene.

15. The process of claim 14 wherein the 6-alkoxy-5-halo1-cyanonaphthalene is a 6-alkoxy-5-iodo-1-cyanonaphthalene.

16. The process of claim 14 wherein the 6-alkoxy-5-iodo1-cyanonaphthalene is 6-methoxy-5-iodo-1-cyanonaphthalene.

17. The process of claim 14 wherein the 6-alkoxy-5-iodo-1-cyanonaphthalene is 6-methoxy-5-bromo-1-cyanonaphthalene.

18. A 6-alkoxy-5-halo-1-cyanonaphthalene.

19. The 6-alkoxy-5-halo-1-cyanonaphthalene of claim 18 wherein the alkoxy substituent is methoxy and the halo substituent is iodo.

20. The 6-alkoxy-5-halo-1-cyanonaphthalene of claim 18 wherein the alkoxy substituent is methoxy and the halo substituent is bromo.

21. The process of claim 1 wherein the compound prepared by trifluoromethylating the 5-halo derivative is a 6-alkoxy-5-trifluoromethyl-1-cyanonaphthalene is 6-methoxy-5-trifluoromethyl-1-cyanonaphthalene.

22. The process of claim 21 wherein the 6-alkoxy-5-trifluoromethyl-1-cyanonaphthalene is 6-methoxy-5-trifluoromethyl-1-cyanonaphthalene.

23. A 6-alkoxy-5-trifluoromethyl-1-cyanonaphthalene.

24. The 6-alkoxy-5-trifluoromethyl-1-cyanonaphthalene of claim 23 wherein the alkoxy substituent is methoxy.

25. The process of claim 1 wherein (1) 6-methoxytetralone is reacted with cyanide ion and a Lewis acid so as to form 6-methoxy-1-cyano-3,4-dihydronaphthalene, (2) the 6-methoxy-1-cyano3,4-dihydronaphthalene is dehydrogenated to 6-methoxy-1-cyanonaphthalene, (3) the 6-methoxy-1-cyanonaphthalene is halogenated so as to form a 6-methoxy-5-halo-1-cyanonaphthalene and then trifluoromethylated to replace the halo substituent with a trifluoromethyl group, and (4) the resultant 6-methoxy-5-trifluoromethyl-1-cyanonaphthalene is hydrolyzed to 6-methoxy-5-trifluoromethyl-1-naphthoic acid.

26. The process of claim 25 wherein the cyanide ion is provided by hydrogen cyanide and the Lewis acid is aluminum chloride.

27. The process of claim 25 wherein the cyanide ion is provided by sodium cyanide and the Lewis acid is aluminum chloride.

28. The process of claim 25 wherein the cyanide ion is provided by sodium cyanide, the Lewis acid is aluminum chloride, and the cyanation is conducted in the presence of an activating amount of water and/or concentrated HCl.

29. The process of claim 25 wherein the 6-methoxy-1-cyanonaphthalene is iodinated so as to form 6-methoxy-5-iodo-1-cyanonaphthalene.

30. The process of claim 25 wherein the 6-methoxy-1-cyanonaphthalene is brominated so as to form 6-methoxy-5-bromo-1-cyanonaphthalene.

* * * * *

UNITED STATES PATENT AND TRADEMARK OFFICE
CERTIFICATE OF CORRECTION

PATENT NO. : 4,590,010
DATED : May 20, 1986
INVENTOR(S) : VENKATARAMAN RAMACHANDRAN ET AL.

It is certified that error appears in the above-identified patent and that said Letters Patent is hereby corrected as shown below:

Column 1, line 44, " corresonding " should read -- corresponding --;

Column 6, line 16, " AlC13 " should read -- $AlCl_3$ --;

Column 7, line 67, " 6-methoxyl- " should read -- 6-methoxy- --;

Column 10, line 14, " halol- " should read -- halo-1- --;

Column 10, line 17, " iodol- " should read -- iodo-1- --;

Column 10, lines 31-32, " is 6-methoxy-5-trifluoromethyl-1-cyanonaphthalene " should not appear.

Signed and Sealed this

Twenty-sixth Day of August 1986

[SEAL]

Attest:

DONALD J. QUIGG

Attesting Officer

Commissioner of Patents and Trademarks